United States Patent [19]

Baralt et al.

[11] Patent Number: 5,780,698
[45] Date of Patent: Jul. 14, 1998

[54] OLEFIN OLIGOMERIZATION CATALYST AND PROCESS EMPLOYING AND PREPARING SAME

[75] Inventors: Eduardo J. Baralt, Kingwood, Tex.; Michael J. Carney, Eldersburg, Md.; Jana B. Cole, Houston, Tex.

[73] Assignee: Chevron Chemical Company, San Ramon, Calif.

[21] Appl. No.: 831,281

[22] Filed: Mar. 31, 1997

[51] Int. Cl.$^6$ .............................. C07C 2/02; B01J 31/00
[52] U.S. Cl. .................... 585/521; 585/520; 585/527; 502/150; 502/152; 502/155; 502/158; 502/162; 502/167
[58] Field of Search .................... 502/150, 152, 502/155, 158, 162, 167; 585/520, 521, 527

[56] References Cited

U.S. PATENT DOCUMENTS

| | | | |
|---|---|---|---|
| 4,668,838 | 5/1987 | Briggs | 585/513 |
| 4,777,315 | 10/1988 | Levine et al. | 585/512 |
| 4,853,356 | 8/1989 | Briggs | 502/117 |
| 4,988,657 | 1/1991 | Martin et al. | 502/158 |
| 5,071,927 | 12/1991 | Benham et al. | 526/64 |
| 5,137,994 | 8/1992 | Goode et al. | 526/75 |
| 5,196,624 | 3/1993 | Threlkel et al. | 585/513 |
| 5,198,563 | 3/1993 | Reagen et al. | 556/57 |

FOREIGN PATENT DOCUMENTS

| | | | |
|---|---|---|---|
| 0 416304 A2 | 3/1991 | European Pat. Off. | C07F 11/00 |
| 0 417477 A2 | 3/1991 | European Pat. Off. | C08F 4/22 |
| 0 537609 A2 | 4/1993 | European Pat. Off. | C07C 2/32 |
| 0 687693 A1 | 12/1996 | European Pat. Off. | C08F 10/00 |

OTHER PUBLICATIONS

D. G. Dick et al., *Inorganic Chemistry*, vol. 32, No. 10, (1993), "Novel Bis (trimethylsilyl)benzamidinato)titanium (III) Complexes", pp. 1959–1962.

*Primary Examiner*—Glenn Caldarola
*Assistant Examiner*—In Suk Bullock
*Attorney, Agent, or Firm*—Marianne H. Michel

[57] ABSTRACT

According to the present invention, a catalyst is provided which is represented by the formula $[RC(YR')_2]_2CrX$, wherein R and R' are individually selected from the group consisting of carbyl and carbylsilyl groups; Y is N, C or P; and X is a halogen, halogen alkyl, Si, alkylsilyl or a carbyl group. Also provided is a process for preparing the catalyst and an oligomerization process employing the catalyst. The process produces linear alpha-olefins with low amounts of polymer, vinylidine and isomerized olefins.

18 Claims, No Drawings

OLEFIN OLIGOMERIZATION CATALYST AND PROCESS EMPLOYING AND PREPARING SAME

FIELD OF THE INVENTION

This invention relates to a catalyst and a process for the oligomerization of olefins employing the catalyst.

BACKGROUND OF THE INVENTION

One significant commercial application of longer chained olefins (e.g., $C_{10}$ to $C_{28}$) is as intermediates in the production of alkyl aromatic sulfonate detergents. Since large amounts of such detergents are ultimately released to the environment, the need for biodegradability is well recognized. It is further well recognized that linear and mono-branched alkyl aromatic sulfonates are generally much more readily biodegraded than multi-branched alkyl aromatic sulfonates and, thus, much more desirable as detergents. Thus, the need exists for processes which efficiently produce high yields of $C_{10}$ to $C_{28}$ linear and/or mono-branched olefins or olefin mixtures which afford biodegradable alkylbenzene sulfonates.

A significant amount of lighter alpha-olefins ($C_{4-8}$) is used in the production of alpha-olefin modified polyethylene resins. The alpha-olefins are used as comonomers with ethylene for the production of high strength and high stress-crack resistant, high density polyethylene. Light alpha-olefins are also used to make linear low-density polyethylene resins (LLDPE). These resins are made by incorporating a higher level of comonomer to reduce the density of linear polyethylene. LLDPE has excellent crack resistance, making it suitable for film applications, overcaps and food containers.

Various chromium catalysts are known for the oligomerization of olefins. Many of these catalysts produce large amounts of polymer product. Other catalysts produce large amounts of light fraction olefins, such as hexene and butene. Still others produce a branched olefin product, vinylidene or a product containing internal double bonds.

For many applications, it is desirable to produce high purity linear alpha-olefins.

SUMMARY OF THE INVENTION

It is an object of the present invention to provide a catalyst capable of oligomerizing olefins.

It is another object of the present invention to provide a catalyst capable of preparing high purity alpha-olefins.

It is another object of the present invention to provide a catalyst capable of preparing high purity linear alpha-olefins.

It is another object of the present invention to provide an economical process for preparing an oligomerization catalyst.

It is another object of the present invention to provide a simple process for preparing an oligomerization catalyst.

It is another object of the present invention to provide a process capable of preparing alpha-olefins containing low amounts of polymer.

It is another object of the present invention to provide a process capable of preparing $C_{4-28}$ alpha-olefins.

It is another object of the present invention to provide a process capable of preparing alpha-olefins containing low amounts of internal double bonds.

It is another object of the present invention to provide a process capable of preparing alpha-olefins containing relatively low amounts of low molecular weight olefins.

It is another object of the present invention to provide a process capable of preparing alpha-olefins containing low amounts of vinylidene.

It is another object of the present invention to provide a process capable of preparing alpha-olefins containing low amounts of branching.

According to the present invention, a catalyst is provided which is represented by the formula $[RC(YR')_2]_2CrX$, wherein R and R' are individually selected from the group consisting of carbyl and carbylsilyl groups; Y is N, C or P; and X is a halogen, halogen alkyl, Si, alkylsilyl or a carbyl group. Also provided is a process for preparing the catalyst and an oligomerization process comprising reacting an olefin feed with the catalyst and a cocatalyst under oligomerization conditions.

DETAILED DESCRIPTION OF THE INVENTION

The catalysts employed in the present invention are chromium +3 organometallic compounds comprising bidentate ligands. As noted above, the catalyst is represented by the formula $[RC(YR')_2]_2CrX$.

R and R' are individually selected from the group consisting of carbyl and carbylsilyl groups. Preferably, R and R' are individually an alkyl containing 1 to 12 carbon atoms, an aryl group containing 6 to 18 carbon atoms, or a trialkyl silyl group, wherein each alkyl group contains 1 to 6 carbon atoms. More preferably, R is an aryl group containing 6 to 12 carbon atoms and R' is a trialkyl silyl group.

Y is N, C or P; preferably, Y is nitrogen.

X is a halogen, halogen alkyl containing 1 to 12 carbon atoms, Si, alkylsilyl containing 1 to 12 carbon atoms or a carbyl group containing 1 to 12 carbon atoms.

The catalysts can be prepared, for example, by the reaction of the appropriate chromium halide complex, such as $CrCl_3THF_3$, with a lithioamidinide complex, such as Li[PhC(NSiMe$_3$)$_2$], where THF is tetrahydrofuran, Ph is a phenyl group, and Me is a methyl group. The product of this reaction is a chromium complex containing two bidentate ligands and can be represented by the formula [PhC(NSiMe$_3$)$_2$]$_2$CrCl. The $CrCl_3THF_3$ can be prepared as described in *Inorganic Synthesis*, 6,129 (1960), the disclosure of which is incorporated herein by reference. The $CrCl_3THF_3$ can also be obtained from Aldrich Chemical Co.

The Li[PhC(NSiMe$_3$)$_2$] can be prepared in a manner similar to that disclosed in Gambarotta et al., *Inorganic Chemistry*, 1993, Vol. 32, No.10 (1959–62), the disclosure of which is incorporated herein by reference. A solution of LiN(SiMe$_3$)$_2$•Et$_2$O in ether is reacted with benzonitrile. LiN(SiMe$_3$)$_2$•Et$_2$O can be prepared by careful dissolution (exothermic reaction) and recrystallization of LiN(SiMe$_3$)$_2$ (Aldrich) from dry diethylether. The solution is stirred for about 4 hours at room temperature. The ether solution containing Li[PhC(NSiMe$_3$)$_2$] is added dropwise to a slurry containing CrCl$_3$(THF)$_3$ in THF. Dark blue crystals of [PhC(NSiMe$_3$)$_2$]$_2$CrCl can be precipitated.

The reaction temperatures for preparing the catalyst can vary broadly, depending on the particular reagents employed. Generally, the reaction temperatures will be in the range of from 0° C. to 200° C., preferably from 25° C. to 125° C., and more preferably from 50° C. to 100° C.

The cocatalyst is an alkali hydrocarbyl silyl compound or a hydrocarbyl aluminum compound. Generally, the hydrocarbyl groups contain from 1 to 12 carbon atoms, preferably from 1 to 8 carbon atoms. Excellent results have been obtained with trimethylsilylmethyllithium and it is preferred.

The hydrocarbyl aluminum compound can be represented by the formula $R''_3Al$, wherein each $R''$ is individually selected and is an alkyl, cycloalkyl, aryl, or hydride radical or two or three $R''$ groups can be joined in a cyclic radical forming a heterocyclic structure. The hydrocarbyl groups contain from 1 to 20 carbon atoms, preferably 1 to 10 carbon atoms.

Examples of suitable $R''$ groups are methyl, ethyl, propyl, isopropyl, butyl, isobutyl, tert-butyl, pentyl, neopentyl, hexyl, 2-methylpentyl, heptyl, octyl, isooctyl, 2-ethylhexyl, 5,5-dimethylhexyl, nonyl, decyl, isodecyl, undecyl, dodecyl, phenyl phenethyl, methoxyphenyl, benzyl, tolyl, xylyl, naphthyl, methylnaphthyl, cyclohexyl, cycloheptyl, and cyclooctyl.

Examples of suitable hydrocarbyl aluminum compounds are as follows: triisobutylaluminum, trihexylaluminum, di-isobutyl aluminum hydride, dihexyl aluminum hydride, isobutyl aluminum dihydride, hexyl aluminum dihydride, di-isobutylhexyl aluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum and triolylaluminum.

Typically, the cocatalyst to catalyst molar ratio is 0.01 to 20, preferably 0.1 to 10.

The catalyst is useful for the oligomerization of olefin feeds. The catalyst can be used to oligomerize olefin feeds comprising olefins containing from 2 to 8 carbon atoms, preferably the olefin feeds are alpha-olefins, especially linear alpha-olefins. Ethylene is especially preferred but other suitable olefins include, but are not limited to, propylene, 1-butene, 1-pentene, 1-hexene, 1-octene, and mixtures thereof. The olefin feed can be a mixture of olefins or a single olefin such as ethylene.

The catalyst and cocatalyst can be contacted with the olefin feed in any convenient manner. One typical method is to dissolve the catalyst and the cocatalyst in a suitable solvent such as a paraffinic, aromatic or an alpha-olefin and introduce the solution into the reactor.

The oligomerization process can be conducted as a batch, continuous, semi-batch or multi-step process. The process can be conducted using suitable equipment in the art.

The reaction conditions for oligomerizing the olefin feed can vary broadly, depending on the catalyst, the desired product, and the olefins employed. They include the temperature and pressure sufficient to produce the desired oligomerized product. Generally, the reaction temperatures will be in the range of from 0° C. to 150° C., preferably from 25° C. to 125° C., and more preferably from 50° C. to 100° C. Generally, the pressure is at least 200 psi, preferably the pressure is greater than 500 psi.

The olefin product comprises a mixture of alpha-olefins containing from 4 to 50 carbon atoms, preferably from 4 to 28. The olefin product contains only trace amounts of vinylidene, branched and isomerized olefins. Less than 1 percent of the olefin product is isomerized. When proper conditions and catalyst are employed, the olefin product contains less than 1000 ppm polymerized olefin.

A typical product distribution for the process is shown below. The product distribution is due to a geometric product distribution [see *Alpha Olefin Handbook* by Lappin et al., page 28].

$C_4$ to $C_8$ content=34%.

$C_{10}$ to $C_{16}$ weight content=25%.

$C_{18}$ to $C_{54}$ weight content=33%.

The olefin products of this invention have established utility in a wide variety of applications such as, for example, surfactants and monomers for use in the preparation of polymers.

The following examples illustrate the invention and are not intended to limit the scope of the invention.

EXAMPLES

Preparation of [PhC(NSiMe$_3$)$_2$]$_2$CrCl

All operations were performed in the absence of water and oxygen (in a glove box or on a Schlenk line). All solvents were distilled from Na/benzophenone solutions (purple) prior to use. LiN(SiMe$_3$)$_2$●Et$_2$O was prepared by careful dissolution (exothermic reaction) and recrystalization of LiN(SiMe$_3$)$_2$ (Aldrich) from dry diethylether. Anhydrous benzonitrile was purchased from Aldrich and used as received. [PhC(NSiMe$_3$)$_2$]$_2$CrCl was prepared by reacting CrCl$_3$(THF)$_3$ with Li[PhC(NSiMe$_3$)$_2$]. The CrCl$_3$(THF)$_3$ was prepared by placing 1 g zinc dust and 20 g (0.13 mol) anhydrous chromium (III) chloride in a 33×80 mm thimble of a Soxhlet extraction apparatus. Approximately 215 mL (2.7 mols) of tetrahydrofuran (freshly distilled from calcium hydride) was placed in a 300 mL round-bottomed flask and attached to the extraction apparatus. A calcium chloride drying tube was fitted to the reflux condenser. At the end of 4 hours of reflux, the reaction was stopped and an additional gram of zinc dust was placed in the thimble. The reflux was then resumed and continued for 8 hours (or until the recycling liquid was colorless). The tetrahydrofuran solution was cooled to room temperature and allowed to stand for at least 12 hours (a calcium chloride drying tube protects the solution from atmospheric moisture). Practically all the tetrahydrofuran was decanted from the precipitated solvate. The purple crystalline product was dried in vacuo at room temperature overnight. The last trace of tetrahydrofuran was removed by pulverizing portions of the product in a mortar under a layer of dry heptane. Suction filtration was used to recover the purple powder. Final drying is effected in vacuo at room temperature. The yield was 113 g, about 86%.

Li[PhC(NSiMe$_3$)$_2$] was prepared by dissolving 5.4048 g (22.4 mmol) LiN(SiMe$_3$)$_2$●Et$_2$O in 100 mL ether and treated dropwise with 2.31 g (22.4 mmol) benzonitrile. The resulting ether solution containing Li[PhC(NSiMe$_3$)$_2$] was stirred for 4 hours at room temperature. The ether solution was added dropwise to a slurry of 4.20 g (11.2 mmol) CrCl$_3$(THF)$_3$ in 50 mL THF. The purple color of CrCl$_3$(THF)$_3$ changed to blue-green after complete addition of Li[PhC(NSiMe$_3$)$_2$]. This solution was stirred for 1 hour after which the solvent was removed under vacuum. The residue was extracted with 50 mL pentane and filtered to remove LiCl. The extraction was repeated until the washings were colorless. The final solution (blue-green) was reduced in volume to about 70 mL, a light blue solid precipitated. Sufficient benzene was added to redissolve the light blue solid and the flask was placed in a –40° C. freezer overnight. The dark blue crystals that formed were collected by filtration and dried under vacuum. The yield was 5.00 g, or 72% of [PhC(NSiMe$_3$)$_2$]$_2$CrCl.

Olefin Oligomerization

In a 500 mL flask equipped with a stirrer were introduced a solvent solution containing 0.165 mmol [PhC(NSiMe$_3$)$_2$]$_2$CrCl. Then 0.16 mmol of trimethylsilylmethyllithium as cocatalyst was introduced. The mixture was stirred for 5 min. Then the catalyst liquor was charged into a 500 cc stainless steel autoclave reactor equipped with a stirrer. The temperature of the autoclave was kept at 55° to 60° C. The stirrer was started, the temperature increased to 75° C., and the pressure increased to 700 psi with ethylene. Samples for gas chromatography analysis were taken after 15 and 30 minutes. After 60 minutes, the ethylene flow was interrupted, the autoclave was rapidly cooled, the unreacted ethylene was removed, and the reaction product totaling 18 grams was discharged from the autoclave. Gas chromatographic analysis showed that the product contained a mixture of linear olefins having from 4 to 30+ carbon atoms. The conversion was about 2,165 lbs NAO/lb chromium cat./hour. Less than 1000 ppm of polyethylene by-product was produced. The resulting NAO fractions had higher alpha-olefin and lower vinylidene olefin than produced NAO fractions using conventional NAO Ziegler-Natta catalysts, Run 107.

Table 1. Runs 101–106, show operating conditions, yields and gas chromatographic analysis of the 1-decene and 1-dodecene fractions for the oligomerization of ethylene using $[PhC(NSiMe_3)_2]_2CrCl$ as catalyst and trimethylsilyl-methyllithium as cocatalyst.

TABLE 1

| Run | Cat./Cocat | Temp. °C. | PSI $C_2H_4$ | Rx Time min. | Yield lbs | % $C_{10}$ alpha-olefin | % $C_{12}$ alpha-olefin |
|---|---|---|---|---|---|---|---|
| 101 | 0.24/0.24 | 75 | 600 | 15 | 2665 | 99.6 | 99.4 |
|  |  |  |  | 30 | 1896 | 99.6 | 99.5 |
|  |  |  |  | 60 | 1242 | 99.5 | 99.4 |
|  |  |  |  | 90 | 2291 | 99.0 | 98.7 |
| 102 | 0.24/0.24 | 70 | 700 | 15 | 5353 | 99.6 | 99.6 |
|  |  |  |  | 30 | 4747 | 99.5 | 99.5 |
| 103 | 0.16/0.15 | 75 | 930 | 15 | 2275 | 100 | 99.6 |
|  |  |  |  | 30 | 1662 | 99.8 | 99.6 |
| 104 | 0.16/0.15 | 75 | 1380 | 15 | 1901 | 100 | 99.8 |
|  |  |  |  | 30 | 1061 | 100 | 99.8 |
| 105 | 0.16/0.15 | 75 | 1420 | 15 | 1107 | 100 | 99.6 |
|  |  |  |  | 30 | 548 | 99.8 | 99.6 |
|  |  |  |  | 60 | 272 | 100 | 99.7 |
| 106 | 0.16/0.15 | 75 | 1420 | 15 | 2671 | 99.8 | 99.7 |
|  |  |  |  | 30 | 1801 | 99.8 | 99.7 |
|  |  |  |  | 60 | 1216 | 99.7 | 99.7 |
| 107 | Chevron Gulftene |  |  |  |  | 96.4 | 95.3 |

The results in Table 1 demonstrate the effectiveness of the inventive catalyst for preparing extremely pure alpha-olefins.

What is claimed is:

1. A catalyst which is represented by the formula $[RC(YR')_2]_2CrX$, wherein R and R' are individually selected from the group consisting of carbyl and carbylsilyl groups; Y is N, C or P; and X is a halogen, halogen alkyl, Si, alkylsilyl or a carbyl group.

2. The catalyst of claim 1 wherein R and R' are individually selected from the group consisting of an alkyl group containing 1 to 12 carbon atoms, an aryl group containing 6 to 18 carbon atoms, and a trialkyl silyl group where each alkyl group contains 1 to 6 carbon atoms.

3. The catalyst of claim 2 wherein each R is an aryl group containing 6 to 12 carbon atoms.

4. The catalyst of claim 3 wherein each R' is trialkyl silyl group where each alkyl group has 1 to 6 carbon atoms.

5. The catalyst of claim 4 wherein Y is nitrogen.

6. The catalyst of claim 5 which is represented by the formula $[PhC(NSiMe_3)_2]_2CrCl$, where Ph is a phenyl group and Me is a methyl group.

7. A process for preparing the catalyst of claim 1 comprising reacting a metal halide complex with a lithioamidinide complex.

8. The process according to claim 7 comprising reacting $CrCl_3THF_3$ with $Li[PhC(NSiMe_3)_2]$, where THF is tetrahydrofuran, Ph is a phenyl group, and Me is a methyl group.

9. An oligomerization process comprising reacting an olefin feed comprising at least one olefin with a catalyst and a cocatalyst under oligomerization conditions to form an olefin product:

wherein the catalyst is represented by the formula $[RC(YR')_2]_2CrX$, wherein R and R' are individually selected from the group consisting of carbyl and carbylsilyl groups; Y is N, C or P; and X is a halogen, halogen alkyl, Si, alkylsilyl or a carbyl group; and wherein the cocatalyst is an alkali hydrocarbyl silyl compound or a hydrocarbyl aluminum compound.

10. The process of claim 9 where less than 1000 ppm polymer are formed.

11. The process of claim 9 wherein the olefin product comprises a mixture of olefins containing from 4 to 50 carbon atoms.

12. The process of claim 11 wherein the olefin product comprises a mixture of olefins containing from 4 to 28 carbon atoms.

13. The process of claim 9 wherein the olefin product comprises alpha-olefins.

14. The process of claim 9 wherein the olefin feed comprises ethylene.

15. The process of claim 14 wherein the olefin product comprises linear alpha-olefins.

16. The process of claim 9 wherein the olefin product contains less than 1 percent isomerization.

17. The process of claim 9 wherein the hydrocarbyl groups in the cocatalyst contain from 1 to 12 carbon atoms.

18. The process of claim 9 wherein the oligomerization conditions include a temperature in the range of from 0° C. to 150° C.

* * * * *